United States Patent [19]

Andel et al.

[11] Patent Number: 5,135,125
[45] Date of Patent: Aug. 4, 1992

[54] HANGING LABEL

[75] Inventors: Dennis J. Andel, Hilton; Jeffrey T. Adams, Rochester, both of N.Y.

[73] Assignee: Tapecon, Inc., Rochester, N.Y.

[21] Appl. No.: 657,154

[22] Filed: Feb. 15, 1991

[51] Int. Cl.$^5$ ............................................. A61M 5/14
[52] U.S. Cl. .................. 215/100 A; 215/12.1; 40/310
[58] Field of Search ............ 215/12.1, 100 A, 100 R, 215/12.2, DIG. 6; 40/310; 229/87.04

[56] References Cited

U.S. PATENT DOCUMENTS

| | | | |
|---|---|---|---|
| 2,135,236 | 11/1938 | Koppelman | 215/12.1 X |
| 2,362,523 | 11/1944 | Armstrong, Jr. et al. | 215/1 R |
| 2,635,604 | 4/1953 | Fredrickson | 128/272 |
| 3,231,919 | 2/1966 | MacDonald | 15/174 |
| 3,635,367 | 1/1972 | Morita et al. | 215/100 A |
| 3,744,658 | 7/1973 | Fujio | 215/100 A |
| 3,893,495 | 7/1975 | Standifer | 215/121 X |
| 4,460,143 | 7/1984 | Ohama | 215/100 A X |
| 4,526,404 | 7/1985 | Vazquez | 40/310 X |
| 4,796,937 | 1/1989 | Andrea | 215/100 A X |
| 4,832,301 | 5/1989 | Hiramoto et al. | 248/359 H |
| 4,948,000 | 8/1990 | Grabenkort | 215/100 A X |

FOREIGN PATENT DOCUMENTS

| | | | |
|---|---|---|---|
| 140420 | 5/1985 | European Pat. Off. | 40/310 |
| 3631021 | 3/1988 | Fed. Rep. of Germany | 40/310 |

*Primary Examiner*—Sue A. Weaver
*Attorney, Agent, or Firm*—Eugene Stephens & Associates

[57] ABSTRACT

A label for identifying contents of intravenous feeding bottles has formed as an integral part thereof a hanging ring for suspending the bottle from an intravenous stand. The label is built up from at least one layer of film, a layer of printing ink, and a layer of adhesive. The handle is defined in the label by a pair of die cut lines that penetrate at least the one layer of film in the label. A release coating is applied between the layer of film and the bottle in a portion of the label defined by the handle to permit the handle to be peeled away from the bottle and the remaining portion of the label.

23 Claims, 1 Drawing Sheet

HANGING LABEL

TECHNICAL FIELD

Our invention relates to the field of labels for pharmaceutical products, particularly intravenous feeding bottles, and of hangers for suspending the intravenous feeding bottles.

DESCRIPTION OF RELATED ART

Pharmaceutical companies apply labels to intravenous feeding bottles to identify their products contained in the bottles and to provide instructions for handling their products. Space is also often provided on the labels to permit health care administrants of the products to write patient information on the labels.

The intravenous feeding bottles are often made of glass that is molded in a special shape for attaching a hanging ring or bail to the base of the bottles. A generally cylindrical shape of the bottles is interrupted by a tapered portion which leaves an annular rim about the base of the bottles. A flexible cap is fit over the rim for attaching a hanging ring or bail to the base of the bottles. The hanging ring is hinged to an end of the cap so that the bottles can be suspended upside down from an intravenous stand.

For example, U.S. Pat. No. 2,635,604 to Fredrickson discloses a cup-shaped member of ductile metal that fits over the bottom of a glass bottle for dispensing intravenous fluids. The cup-shaped member includes a lip that fits within an annular groove formed in the bottle near its base. The end of the cap is cut out in a pattern leaving a handle portion that can be bent away from the remaining portion of the cap for suspending the bottle.

The special molding requirements for the intravenous bottles and the separate caps required to suspend them add considerable incremental cost to administering intravenous fluids to patients. The task of attaching the hanging caps to bottles takes time and may delay dispensing medication to patients if appropriately sized caps are not readily available.

U.S. Pat. No. 3,635,367 to Morita et al. and U.S. Pat. No. 3,744,658 to Fujio disclose permanently mounted hanging rings for suspending intravenous bottles. Their respective hanging rings are formed in disk-shaped members that fit against the bottom of intravenous bottles and are secured thereto by protective liners. The disks are made of a rubber-like material that permits the hanging rings to be bent away from the bottom of the bottles. The protective liners are made from a resin material that is heat-contracted over portions of the sides and bottom of the bottles. Outer portions of the disks are also encased within the liners for permanently attaching the hanging rings to the bottles. The protective liners may also be used to attach labels to the sides of the bottles.

Although such permanently mounted hangers are more convenient to use than separately assembled bottles and hanger caps, considerable incremental cost is added to the bottles by requiring an additional manufacturing step of applying a "shrink-wrap" liner. The plastic material for the liners is particularly costly in comparison with the cost of the glass out of which the bottles are made.

SUMMARY OF THE INVENTION

Our invention overcomes the above-identified problems with attaching hanging rings to intravenous bottles by incorporating the hanging rings as integral parts of labels for the intravenous bottles. The labels may be constructed from conventional label-making materials, and the hanging rings may be cut out of the label stock at very little expense over the cost of the label. Also, the considerable costs of separately manufacturing and attaching the hanging rings are eliminated.

Our label includes at least one layer of film, to which a layer of printing ink and a layer of adhesive are applied. The printing ink is used to identify the contents of the bottle or display other relevant information concerning the bottle's contents. The adhesive is used to attach the label to the bottle. A hanging ring or similar form of handle is formed in a portion of the label by a pattern of cuts in the layer of film. A release coating is applied between the bottle and the layer of film within the pattern of cuts which define the hanging ring. Ends of the hanging ring are joined to the bottle by uncut portions of the film and a remaining portion of the adhesive layer that is not covered with the release coating. An arcuate portion of the hanging ring extending between between its two ends may be peeled apart from the remaining portion of the label for suspending the bottle from a conventional intravenous feeding stand.

The two ends of the hanging ring are formed in portions of the label which are intended to cover opposite diametrical surfaces of the intravenous bottle. The annular portion of the hanging ring extends in the label towards the top of the bottle. However, the hanging ring may be peeled apart from the label and folded against its two ends to fit over the bottom of the bottle with sufficient clearance to hang the bottle upside down from a conventional fixture. The hanging ring may be joined at its ends to the remaining portion of the label with curved lines that are also cut through the film. The curves gradually widen the ends of the handle to relieve sheering stresses between the handle and label.

Preferably, the label, out of which the hanging ring is cut, is made of conventional label stock including two layers of film, two layers of adhesive, and two layers of printing ink. One of the layers of film may be made of an acetate material forming a base layer of the label. A first layer pressure-sensitive adhesive is applied to a bottom surface of the base layer of film for attaching the label to a bottle. One of the layers of printing ink is applied to a top surface of the base layer as a homogeneous layer of ink forming a base color of the label. The other layer of ink is applied as a discontinuous layer of differently colored ink over the base color ink for displaying desired information. A second layer of pressure-sensitive adhesive is applied to the layers of printing ink for attaching the other of the layers of film. The other layer of film protects the printing ink from wear but is made transparent to expose the printing ink to view, and may include a matte finish that can be written on by conventional writing instruments.

The hanging ring is cut through the layer of transparent film, the second layer of adhesive, and both layers of printing ink. Within a portion of the label outlined by the hanging ring, a release lacquer is applied between the printing ink and the base layer of acetate film. The lacquer adheres to the printing ink, but does not form a bond with the acetate film. Accordingly, when the hanging ring is peeled away from the remaining portion of the label, the layers of printing ink are protected on one side by the transparent film and on the other side by the lacquer. The base layer of acetate film beneath the hanging ring portion remains bonded to the bottle.

The layer of transparent film must be made of a material that is strong enough to support the bottle. However, it is also important that the transparent film is able to stretch without breaking so that the hanging ring can be initially peeled away from the circumference of the bottle. Polypropylene film has been found to be effective for this purpose. The hanging ring may also include a tab from which to start peeling the hanging ring from the label. The tab is located along an edge of the handle in a position that directs at least a portion of the initial peeling force along a tangent line to the bottle's circumference.

Nothing more than a small amount of lacquer is required of materials for constructing our label to incorporate a hanging ring for suspending intravenous bottles. Further, only two easy manufacturing steps are required to improve upon conventional label making to incorporate the hanging ring. One of the steps is to apply the lacquer, and the other step involves a die cutting operation that is commonplace in label manufacture.

DRAWINGS

DETAILED DESCRIPTION

Figure 1:
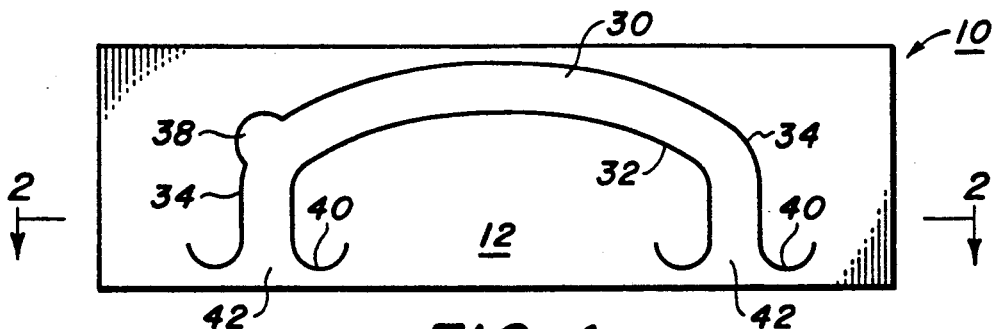
FIG. 1 is a plan view of our preferred label showing a hanging ring cut through a front face of the label.
Figure 2:
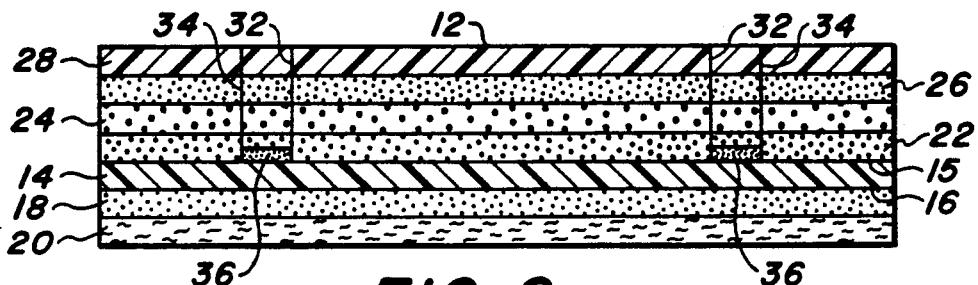
FIG. 2 is a greatly enlarged cross-sectional view of our label taken generally along line 2—2 of FIG. 2 and showing the layers of material from which the label is constructed.

A preferred embodiment of our new label 10 is shown in the first two drawing figures. The label 10 is built up from several layers of materials that are demarcated in the enlarged cross-sectional view of FIG. 2.

A base layer of acetate film 14 includes front and back surfaces 15 and 16, respectively. A layer of pressure-sensitive adhesive 18 is applied to the back surface 16 of base layer 14. A kraft liner 20 protects the adhesive layer 18 until the label is ready to be mounted on a bottle. Two layers of printing ink designated as 22 and 24 are applied to front surface 15 of the base layer. The layer 22 is a homogeneous layer of white ink that forms a background color of the label. Graphics and printed information are applied in discontinuous layer 24 of differently colored ink. A second layer of pressure-sensitive adhesive 26 is applied to the layers of printing ink bonding a layer 28 of transparent film to form a front surface 12 of the label 10.

Hanging ring 30 is die cut through the front surface 12 of the label along inner and outer penetrating lines 32 and 34, respectively. Both of the lines 32 and 34 penetrate the layer of transparent film 28, the second layer of pressure-sensitive adhesive 26, and the two layers of printing ink 22 and 24. Within the outline of the hanging ring 30 cut by lines 32 and 34, a layer of release lacquer 36 is applied between the layer 22 of printing ink and the base layer 14 of acetate film. The release lacquer 36 bonds to the layer of printing ink but does not adhere to the front surface 15 of the acetate film.

A tab 38 is formed by outer penetrating line 34 to provide a convenient location to begin peeling the hanging ring 30 away from the remaining portion of the label. The location of the tab 38 is also selected so that a significant portion of the initial peeling force is directed along a tangent to the circumference of the bottle to minimize the amount that the film layer 28 must be stretched to start peeling the hanging ring.

The penetrating lines 32 and 34 also terminate with stress relief curves 40 that join ends 42 of the hanging ring to the label. Both transparent film layer 28 and the second adhesive layer 26 participate in joining the hanging ring to the remaining portion of the label. Preferably, the release coating is applied along only portions of the curves 40 nearest the handle ends 42 to assure that the ends remain securely attached to the remaining portion of the label. Elsewhere, it is possible for the release coating to overlap portions of the label adjacent to the hanging ring without significant consequence.

Figure 3:
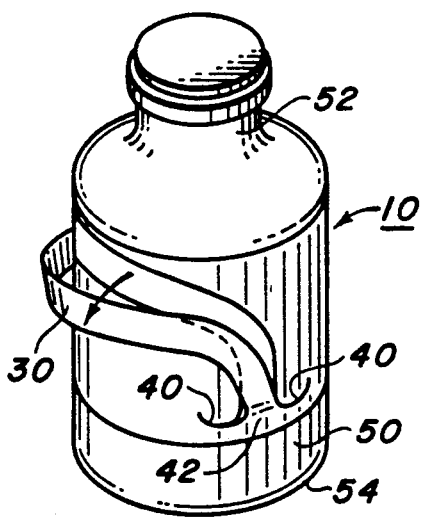
FIG. 3 is a perspective view of an intravenous bottle with our hanging ring partially peeled away from the remaining label.
Figure 4:
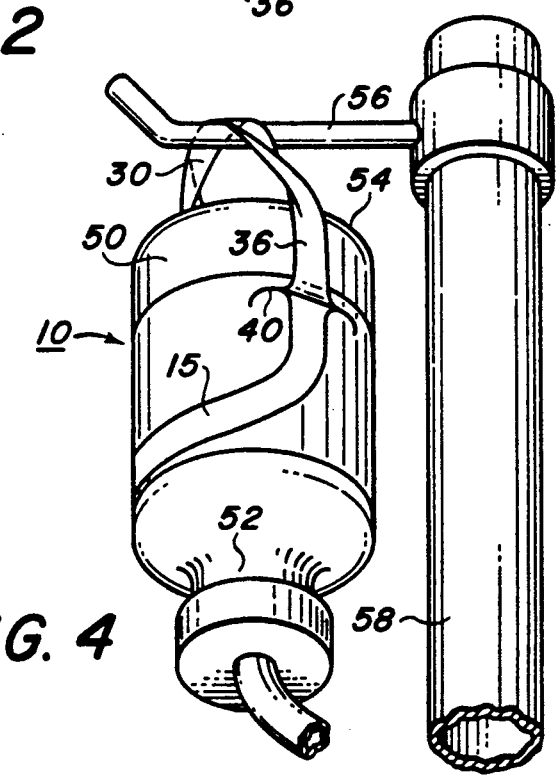
FIG. 4 is a perspective view of the intravenous feeding bottle suspended from our label on an intravenous feeding fixture.

In FIG. 3, the label 10 is mounted on the cylindrical surface of an intravenous feeding bottle 50. Kraft liner 20 is removed exposing the first adhesive layer 18 for bonding the label to the bottle. The ends 42 of the hanging ring are located on opposite diametrical sides of the bottle, and the hanging ring projects vertically from its ends within the label toward the top portion 52 of the bottle. However, the hanging ring may be peeled away from the remaining portion of the label and folded against its ends as shown in FIG. 4 for pivoting the hanging ring over the base 54 of the bottle.

The layer of transparent film 28 is preferably made from polypropylene or similar material that is capable of stretching without breaking. Forces directed away from the cylindrical surface of the bottle 50 stretch the polypropylene material of the hanging ring by an amount which permits the hanging ring to be peeled back from the surface of the bottle. Two functions are served by this feature. First, the hanging ring remains securely held within the label until the hanging ring is initially stretched away from the bottle. Second, once stretched, the hanging ring leaves a permanent record of the bottle's use. The layer of transparent film 28 is also preferably made with a matte finish so that it can be written on by conventional writing instruments.

Handling ring 30 is also dimensioned in the label with respect to the location of its ends 42 from the base 54 of the bottle so that at least a small amount of clearance is provided between the hanging ring and bottle base. In the view of FIG. 4, hook 56 of intravenous stand 58 is inserted between the hanging ring and bottle base for suspending the bottle upside down from hanging ring 30 on hook 56.

Figure 5:
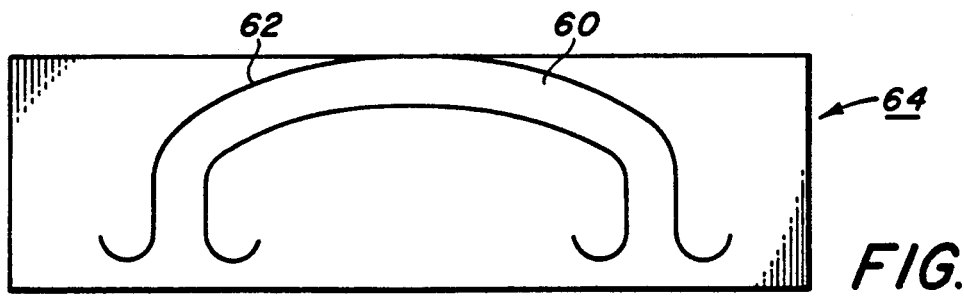
FIG. 5 is a plan view of an alternatively cut out hanging ring that intersects a top edge of the label.

A variation of the embodiment illustrated in the preceding figures is shown in FIG. 5. Instead of providing a tab for initially peeling a hanging ring away from the remaining portion of the label, a hanging ring 60 is formed, in part, by outer cut line 62 that intersects the periphery of label 64. Thus, the outer line 62 of the hanging ring is exposed at its intersection with the label periphery. Appropriate instructions can also be printed on the label to indicate where the hanging ring can be most easily peeled away from the rest of the label.

Our label can be manufactured using conventional operations that are commonplace in the art. However, in addition to the usual steps of label manufacture, selected outer layers of the label are die cut in a conventional operation to define a hanging ring or other similar handle shape as an integral part of the label. A release coating is applied between selected layers of the label in the portion of the label cut out for use as a handle. Preferably, the release coating is applied between the printing inks and base film layers of the label so that the ink is removed with the handle, but remains protected on the handle by the release coating. The printing ink also makes the handle easy to see for draping the handle over hook 56 of an intravenous feeding stand 58.

We claim:

1. In a label for identifying contents of intravenous feeding bottles, the label being of the type including:
   a base layer of film having front and back surfaces;
   a first layer of pressure-sensitive adhesive applied to said back surface of the base layer;
   a layer of printing ink applied to said front surface of the base layer;
   a second layer of pressure-sensitive adhesive applied to said layer of printing ink; and
   a layer of transparent film applied to said second layer of pressure-sensitive adhesive; the improvement in which:
   said layer of printing ink, said second layer of pressure-sensitive adhesive, and said layer of transparent film are penetrated by a pattern of cuts in the form of a hanging ring for suspending an intravenous feeding bottle in an inverted position; and
   a release coating is applied between said base layer and said layer of printing ink within said pattern of cuts that form said hanging ring for permitting said hanging ring to be peeled apart from the remaining portion of the label.

2. The label of claim 1 in which said release coating adheres to said layer of printing ink but does not adhere to said base layer of film.

3. The label of claim 2 in which said transparent film is stretchable so that said hanging ring can be peeled away from said remaining portion of the label when the label is attached to a cylindrical outer surface of the intravenous bottle.

4. The label of claim 3 wherein said layer of printing ink, said layer of pressure-sensitive adhesive, and said layer of transparent film of the label are also penetrated by cuts in the form of stress relief curves joining ends of said hanging ring to said remaining portion of the label.

5. The label of claim 4 wherein said ends of the hanging ring are positioned with respect to said remaining portion of the label for attaching said hanging ring to opposite diametrical sides of the intravenous bottles.

6. The label of claim 5 wherein said hanging ring is sized to provide clearance between said hanging ring and the base of the intravenous bottles for suspending the intravenous bottles from an intravenous stand.

7. The label of claim 6 wherein said hanging ring includes an integrally formed tab to assist peeling of said hanging ring away from said remaining portion of said label.

8. The label of claim 6 wherein said hanging ring forms a part of a peripheral surface of the label to assist peeling of said hanging ring away from said remaining portion of said label.

9. The label of claim 6 wherein said layer of transparent film includes a matte finish that can be written on by conventional writing instruments.

10. The label of claim 9 wherein said layer of printing ink includes a homogeneous layer of colored ink forming a base color of the label and a discontinuous layer of differently colored ink for displaying product identifying information.

11. The label of claim 10 wherein said discontinuous layer includes instructions for using products that are printed in said remaining portion of the label so that said instructions are not obscured by peeling said hanging ring away from said remaining portion of the label.

12. The label of claim 6 wherein said first layer of pressure-sensitive adhesive is protected by a kraft liner prior to mounting the label onto the intravenous bottle.

13. The label of claim 12 wherein said base layer is formed from an acetate film.

14. The label of claim 13 wherein said transparent layer is formed from a polypropylene film.

15. The label of claim 6 wherein said release coating is not applied along a portion of the length of said stress relief curves so that said ends of the hanging ring are also joined to said base layer by said second layer of pressure-sensitive adhesive.

16. The label of claim 15 wherein said release coating is in the form of a lacquer.

17. A hanger for suspending a bottle comprising:
   a label for identifying contents of the bottle having formed as an integral part thereof a handle and including means for peeling said handle away from the remaining portion of the label;
   said label including a layer of adhesive for affixing said label to a cylindrical surface of an intravenous bottle, a layer of printing ink for displaying information regarding the bottle's contents, and at least one layer of film providing for structural integrity of said label; and
   said handle being formed by cuts through said one layer of film defining two ends that are positioned in said label for attaching said handle to opposite diametrical sides of the bottle and an annular portion that is sized to provide clearance between said handle and an end of the bottle for suspending the bottle on a fixture.

18. The hanger of claim 17 in which said handle is defined by inner and outer cuts that terminate with stress relief curves at said two ends of the handle.

19. The hanger of claim 18 in which said one layer of film is made transparent to expose said printing ink to view.

20. The hanger of claim 19 in which said one layer of film is made stretchable to permit said one layer film to be peeled away from the cylindrical surface of the bottle.

21. The hanger of claim 20 wherein said peeling means includes a release coating is applied between said layer of printing ink and the cylindrical surface of the bottle in a portion of said label defined by said handle.

22. The hanger of claim 21 in which said layer of printing ink in said portion of the label defined by the handle is protected on one side by said one layer of film and on the other side by said release coating.

23. The hanger of claim 22 in which said release coating is applied to a second layer of film that attaches to the cylindrical surface of the bottle with a second layer of adhesive.

* * * * *